(12) United States Patent
Looker et al.

(10) Patent No.: US 7,354,966 B2
(45) Date of Patent: Apr. 8, 2008

(54) COMPOUNDS FOR USE AS SURFACTANTS

(75) Inventors: Brian Edgar Looker, Stevenage (GB); Christopher James Lunniss, Stevenage (GB); Alison Judith Redgrave, Stevenage (GB)

(73) Assignee: Glaxo Group Limited, Greenford, Middlesex (GB)

( * ) Notice: Subject to any disclaimer, the term of this patent is extended or adjusted under 35 U.S.C. 154(b) by 191 days.

(21) Appl. No.: 10/506,339

(22) PCT Filed: Mar. 4, 2003

(86) PCT No.: PCT/GB03/00876

§ 371 (c)(1), (2), (4) Date: May 11, 2005

(87) PCT Pub. No.: WO03/074537

PCT Pub. Date: Sep. 12, 2003

(65) Prior Publication Data

US 2005/0287076 A1  Dec. 29, 2005

(30) Foreign Application Priority Data

Mar. 6, 2002 (GB) ................................. 0205327.0

(51) Int. Cl.
| | |
|---|---|
| A61K 31/00 | (2006.01) |
| A61K 47/28 | (2006.01) |
| A61K 9/00 | (2006.01) |
| A61K 9/10 | (2006.01) |
| A61K 9/12 | (2006.01) |
| A61K 9/14 | (2006.01) |
| C01B 25/00 | (2006.01) |
| C07F 9/00 | (2006.01) |
| C07F 9/09 | (2006.01) |
| C07F 9/10 | (2006.01) |

(52) U.S. Cl. ..................... 524/145; 424/45; 424/46; 424/489; 514/136; 514/141; 423/309; 554/76

(58) Field of Classification Search ............... 424/45, 424/46; 554/78, 79, 80
See application file for complete search history.

(56) References Cited

U.S. PATENT DOCUMENTS 4,352,789 A   10/1982  Thiel
5,126,123 A   6/1992   Johnson
5,376,359 A   12/1994  Johnson
6,413,543 B1 *  7/2002  Eibl ........................... 424/450
6,451,287 B1   9/2002   Desimone et al.

FOREIGN PATENT DOCUMENTS

| EP | 0372777 | 6/1990 |
|---|---|---|
| WO | 91/04011 | 4/1991 |
| WO | 91/11173 | 8/1991 |
| WO | 91/11495 | 8/1991 |
| WO | 91/14422 | 10/1991 |
| WO | 92/00062 | 1/1992 |
| WO | 96/32099 | 10/1996 |

OTHER PUBLICATIONS

Lacy, C.; Armstrong, L. L.; Lipsy, R. J.; Lance, L. L. Drug Information Handbook, Lexi-Comp, Inc.: Cleveland, 1999, pp. 32-34, 112-114, 253-254, 259-260, 262-263, 319-321, 547-549, 781-785.*

MERCK online Manual home edition online articles entitled, Bronchopulmonary Dysplasia (BPD); "Langerhan's Cell Granulomatosis"; "Respiratory Tract Infections"; "Pulmonary Embolism(PE)", and "Lung Cancer"—accessed May 14, 2007.*

The Merriam-Webster's Collegiate Dictionary, 10th edition, Merriam-Webster Incorporated: Springfield, Massachusetts, 1993, pp. 311.*

* cited by examiner

*Primary Examiner*—Sreeni Padmanabhan
*Assistant Examiner*—James H Alstrum-Acevedo
(74) *Attorney, Agent, or Firm*—Bonnie L. Deppenbrock

(57) ABSTRACT

Compounds of formula (I):

(I)

$$R^{1b}-\overset{R^{1a}}{\underset{R^{1c}}{N^+}}-\text{CH}_2\text{CH}_2-O-\overset{O}{\underset{O^-}{P}}-O-\text{CH}_2-\text{CH}(O-Y^1-[P(O)(OR^2)-O-X^1]_n-OR^2)-\text{CH}_2-O-Y^2-[O-X^2]_q-OR^3$$

and uses of such compounds are described.

20 Claims, No Drawings

COMPOUNDS FOR USE AS SURFACTANTS

This application is filed pursuant to 35 U.S.C. § 371 as a United States National Phase Application of International Patent Application Ser. No. PCT/GB03/00876 filed Mar. 4, 2003, which claims priority from Great Britain Application No. 0205327.0 filed in the United Kingdom on Mar. 6, 2002.

This invention relates to novel surfactants and aerosol formulations thereof for use in the administration of medicaments by inhalation.

The use of aerosols to administer medicaments has been known for several decades. Such aerosols generally comprise the medicament, one or more chlorofluorocarbon propellants and either a surfactant or a co-solvent, such as ethanol. The most commonly used aerosol propellants for medicaments have been propellant 11 ($CCl_3F$) and/or propellant 114 ($CF_2ClCF_2Cl$) with propellant 12 ($CCl_2F_2$). However these propellants are now believed to provoke the degradation of stratospheric ozone and there is thus a need to provide aerosol formulations for medicaments which employ so called "ozone-friendly" propellants.

A class of propellants which are believed to have minimal ozone-depleting effects in comparison to conventional chlorofluorocarbons comprise fluorocarbons and hydrogen-containing chlorofluorocarbons, and a number of medicinal aerosol formulations using such propellant systems are disclosed in, for example, EP0372777, WO91/04011, WO91/11173, WO91/11495 and WO91/14422. These applications are all concerned with the preparation of pressurised aerosols for the administration of medicaments and seek to overcome the problems associated with the use of the new class of propellants, in particular the problems of stability associated with the pharmaceutical formulations prepared. The applications all propose the addition of one or more of adjuvants such as alcohols, alkanes, dimethyl ether, surfactants (including fluorinated and non-fluorinated surfactants, carboxylic acids, polyethoxylates etc) and even conventional chlorofluorocarbon propellants in small amounts intended to minimise potential ozone damage.

It is essential that the prescribed dose of aerosol medication delivered from the MDI to the patient consistently meets the specifications claimed by the manufacturer and comply with the requirements of the FDA and other regulatory authorities. That is, every dose delivered from the can must be the same within close tolerances. Therefore it is important that the formulation be substantially homogenous throughout the administered dose at the time of actuation of the metering valve.

In the case of suspension formulations, to control aggregation of fine particles and thereby influence the dispersability of the suspension, it is well established in the art that fluorinated surfactants may be used to stabilise micronised drug suspensions in fluorocarbon propellants such as 1,1,1, 2-tetrafluoroethane (P134a) or 1,1,1,2,3,3,3-heptafluoro-n-propane (P227), see for example U.S. Pat. No. 4,352,789, U.S. Pat. No. 5,126,123, U.S. Pat. No. 5,376,359, U.S. application Ser. No. 09/580008, WO91/11173, WO91/14422, WO92/00062, and WO96/09816. WO92/00061 discloses non-fluorinated surfactants for use with fluorocarbon propellants.

Surprisingly, the applicants have now found that a particular group of novel non-fluorinated and low fluorine content compounds with good surfactant properties may be used to prepare novel aerosol formulations, and can be advantageous in terms of improving the stability of the aerosol formulation, reducing drug deposition, increasing shelf life and the like. In addition the compounds of the invention are adequately soluble in the fluorocarbon or hydrogen-containing chlorofluorocarbon propellants or mixtures thereof, obviating the need to use a polar adjuvant.

Thus, in one aspect the invention provides a compound of the general formula (I)

(I)

[Chemical structure of formula (I) showing:
$R^{1b}$—$N^+$($R^{1a}$)($R^{1c}$)—$CH_2CH_2$—O—P(=O)(O$^-$)—O—CH($CH_2$—O—$Y^1$—(C($R^4$))$_p$—[O—$X^1$]$_n$—O$R^2$)—($CH_2$—O—$Y^2$—(C($R^5$))$_q$—[O—$X^2$]$_m$—O$R^3$)]

or a salt or solvate thereof wherein:

m, n, p and q independently represent an integer 1 to 12;

$R^{1a}$, $R^{1b}$ and $R^{1c}$ independently represent $C_{1-3}$ alkyl or hydrogen;

$R^2$ and $R^3$ independently represent $C_{1-4}$ alkyl optionally substituted with up to 5 fluorine atoms or —$COC_{1-2}$ alkyl optionally substituted with up to 5 fluorine atoms;

$R^4$ and $R^5$ independently represent —$CH_3$ or hydrogen.

$X^1$ and $X^2$ independently represent —($CH_2$)$_2$—, —(C$H_2$)$_3$—, —$CH(CH_3)CH_2$—, —$CH_2CH(CH_3)$—, —$CH(CH_3)CH_2CH_2$, —$CH_2CH(CH_3)CH_2$—, $CH_2CH_2CH(CH_3)$ or —$COCH(CH_3)$ —; and $Y^1$ and $Y^2$ independently represent —$CH_2$— or carbonyl;

with the proviso that when:

p and q represent 1; and m and n independently represent an integer between 1 to 12; and $R^4$ and $R^5$ represent hydrogen; and $X^1$ and $X^2$ represent —($CH_2$)$_2$—; and $Y^1$ and $Y^2$ represent —$CH_2$—; then $R^2$ and $R^3$ may only independently represent $C_{1-2}$ alkyl optionally substituted with up to 5 fluorine atoms or —$COC_{1-2}$ alkyl optionally substituted with up to 5 fluorine atoms.

Preferably n and m independently represent an integer 2 to 8, especially 3 to 6.

Preferably p and q independently represent an integer 1 to 6, especially 1 to 3, particularly 1.

Preferably $R^{1a}$ represents methyl. Preferably $R^{1b}$ represents methyl. Preferably $R^{1c}$ represents methyl. Preferably $R^{1a}$ represents the same as $R^{1b}$ and $R^{1c}$.

Preferably neither $R^2$ nor $R^3$ represents —$COCFH_2$. Preferably $R^2$ and $R^3$ independently represent —$COCH_3$, —$COCH_2CH_3$, $C_{1-3}$alkyl (e.g. methyl, ethyl, propyl or isopropyl), —$CHF_2$, $CF_3$ or —$CH_2CF_3$, more preferably —$CH_3$, —$CF_3$ or —$CH_2CF_3$, especially —$CH_3$ or —$CH_2CF_3$, most especially —$CH_2CF_3$.

Preferably $R^4$ and $R^5$ represent hydrogen.

Preferably $Y^1$ represents carbonyl. Preferably $Y^2$ represents carbonyl.

Most preferably n will represent the same as m. Most preferably p will represent the same as q. Most preferably $R^{1a}$, $R^{1b}$ and $R^{1c}$ represent —$CH_3$. Most preferably $R^2$ will represent the same as $R^3$. Most preferably $R^4$ will represent the same as $R^5$. Most preferably $X^1$ will represent the same as $X^2$. Most preferably $Y^1$ will represent the same as $Y^2$.

In a first preferred series of compounds:

p and q independently represent 1 to 3;

$R^2$ and $R^3$ independently represent $C_{1-4}$ alkyl optionally substituted with up to 5 fluorine atoms or —$COC_{1-2}$ alkyl optionally substituted with up to 5 fluorine atoms, preferably —$COCH_3$ or —$COCH_2CH_3$, especially —$COCH_3$;

$R^4$ and $R^5$ independently represent hydrogen or —$CH_3$, preferably —$CH_3$;

$X^1$ and $X^2$ represent —$COCH(CH_3)$—; and $Y^1$ and $Y^2$ represent carbonyl.

In a second series of preferred compounds:

p and q independently represent 1 to 3;

$R^2$ and $R^3$ independently represent $C_{1-4}$ alkyl optionally substituted with up to 5 fluorine atoms or —$COC_{1-2}$ alkyl optionally substituted with up to 5 fluorine atoms, preferably $C_{1-3}$ alkyl, —$CHF_2$, —$CF_3$ or —$CH_2CF_3$, more preferably —$CH_3$, —$CF_3$, —$CH_2CH_3$ or —$CH_2CF_3$, especially —$CH_3$ or —$CH_2CF_3$, most especially —$CH_2CF_3$;

$R^4$ and $R^5$ independently represent hydrogen or methyl, preferably hydrogen;

$X^1$ and $X^2$ preferably independently represent —$(CH_2)_2$—, —$(CH_2)_3$—, —$CH(CH_3)$ $CH_2$—, —$CH_2CH(CH_3)$—, —$CH(CH_3)CH_2CH_2$—, —$CH_2CH(CH_3)CH_2$— or $CH_2CH_2CH(CH_3)$—, preferably —$(CH_2)_2$—, —$CH(CH_3)CH_2$— or —$CH_2CH(CH_3)$—, especially —$(CH_2)_2$—; and $Y^1$ and $Y^2$ independently represent —$CH_2$— or carbonyl, especially carbonyl.

Compounds of formula (I) contain one or more chiral centres. It will be understood that compounds of formula (I) include all optical isomers of the compounds of formula (I) and mixtures thereof, including racemic mixtures thereof.

Compounds of formula (I) may exist in the form of salts or solvates, which also form an aspect of the invention. Examples of salts include acid addition salts e.g. hydrogen chloride or hydrogen bromide. Examples of solvates include hydrates.

In a further aspect the invention provides a pharmaceutical aerosol formulation which comprises particulate medicament, a fluorocarbon or hydrogen-containing chlorofluorocarbon propellant, or mixtures thereof, and a compound of formula (I) or salt or solvate thereof as described above.

The compounds of formula (I) employed for the preparation of formulations according to the present invention are effective stabilisers at low concentrations relative to the amount of medicament. Thus, the amount of compound of formula (I) employed is desirably in the range of 0.05% to 20% w/w, particularly 0.5% to 10% w/w, more particularly 0.5% to 5% w/w, relative to the medicament.

The particle size of the particulate (e.g. micronised) medicament should be such as to permit inhalation of substantially all of the medicament into the lungs or nasal cavity upon administration of the aerosol formulation and will thus be less than 100 microns, desirably less than 20 microns, and preferably will have a mass median aerodynamic diameter (MMAD) in the range 1-10 microns, e.g. 1-5 microns.

The final aerosol formulation desirably contains 0.005-10% w/w, preferably 0.005-5% w/w, especially 0.01-1.0% w/w, of medicament relative to the total weight of the formulation.

Medicaments which may be administered in aerosol formulations according to the invention include any drug useful in inhalation therapy and which may be presented in a form which is substantially completely insoluble in the selected propellant. Appropriate medicaments may thus be selected from, for example, analgesics, e.g. codeine, dihydromorphine, ergotamine, fentanyl or morphine; anginal preparations, e.g. diltiazem; anti-allergics, e.g. cromoglycate (e.g. as sodium salt), ketotifen or nedocromil (e.g. as sodium salt); anti-infectives e.g. cephalosporins, penicillins, streptomycin, sulphonamides, tetracyclines and pentamidine; anti-histamines, e.g. methapyrilene; anti-inflammatories, e.g. beclomethasone (e.g. as dipropionate), fluticasone (e.g. as propionate), flunisolide, budesonide, rofleponide, mometasone (e.g. as furoate), ciclesonide, triamcinolone (e.g. as acetonide) or 6α, 9α-difluoro-11β-hydroxy-16α-methyl-3-oxo-17α-propionyloxy-androsta-1,4-diene-17β-carbothioic acid S-(2-oxo-tetrahydro-furan-3-yl) ester; anti-tussives, e.g. noscapine; bronchodilators, e.g. albuterol (e.g. as free base or as sulphate), salmeterol (e.g. as xinafoate), ephedrine, adrenaline, fenoterol (e.g. as hydrobromide), formoterol (e.g. as fumarate), isoprenaline, metaproterenol, phenylephrine, phenylpropanolamine, pirbuterol (e.g. as acetate), reproterol (e.g. as hydrochloride), rimiterol, terbutaline (e.g. as sulphate), isoetharine, tulobuterol, 4-hydroxy-7-[2-[[2-[[3-(2-phenylethoxy)propyl]sulfonyl]ethyl]amino]ethyl-2 (3H)-benzothia-zolone; diuretics, e.g. amiloride; anti-cholinergics, e.g. ipratropium (e.g. as bromide), tiotropium, atropine or oxitropium; hormones, e.g. cortisone, hydrocortisone or prednisolone; xanthines, e.g. aminophylline, choline theophyllinate, lysine theophyllinate or theophylline. It will be clear to a person skilled in the art that, where appropriate, the medicaments may be used in the form of salts, (e.g. as alkali metal or amine salts or as acid addition salts) or as esters (e.g. lower alkyl esters) or as solvates (e.g. hydrates) to optimise the activity and/or stability of the medicament and/or to minimise the solubility of the medicament in the propellant. It will be further clear to a person skilled in the art that where appropriate, the medicaments may be used in the form of a pure isomer, for example, R-albuterol or R,R-formoterol.

Particularly preferred medicaments for administration using aerosol formulations in accordance with the invention include anti-allergics, bronchodilators and anti-inflammatory steroids for use in the treatment of respiratory disorders such as asthma, COPD or rhinitis by inhalation therapy, for example cromoglycate (e.g. as sodium salt), albuterol (e.g. as free base or sulphate), salmeterol (e.g. as xinafoate), formoterol (e.g. as fumarate), terbutaline (e.g. as sulphate), reproterol (e.g. as hydrochloride), a beclomethasone ester (e.g. as dipropionate), a fluticasone ester (e.g. as propionate). Salmeterol, especially salmeterol xinafoate, albuterol sulphate, fluticasone propionate, beclomethasone dipropionate and physiologically acceptable salts and solvates thereof are especially preferred.

It will be appreciated by those skilled in the art that the aerosol formulations according to the invention may, if desired, contain a combination of two or more active ingredients. Thus suitable combinations include bronchodilators (e.g. albuterol or isoprenaline) in combination with an anti-inflammatory steroid (e.g. beclomethasone ester); a bronchodilator in combination with an anti-allergic (e.g. cromoglycate). Exemplary combinations also include: ephedrine and theophylline; fenoterol and ipratropium; isoetharine and phenylephrine; albuterol (e.g. as free base or as sulphate) and a beclomethasone ester (e.g. dipropionate); budesonide and formoterol (e.g. as fumarate) which is of particular interest; and salmeterol (particularly as salmeterol xinafoate) and a fluticasone ester (e.g. propionate) also of particular interest.

The propellants for use in the invention may be any fluorocarbon or hydrogen-containing chlorofluorocarbon or mixtures thereof having a sufficient vapour pressure to render them effective as propellants. Preferably the propellant will be a non-solvent for the medicament. Suitable propellants include, for example, $C_{1-4}$ hydrogen-containing chlorofluorocarbons such as $CH_2ClF$, $CClF_2CHClF$, $CF_3CHClF$, $CHF_2CClF_2$, $CHClFCHF_2$, $CF_3CH_2Cl$ and $CClF_2CH_3$; $C_{1-4}$ hydrogen-containing fluorocarbons such as $CHF_2CHF_2$, $CF_3CH_2F$, $CHF_2CH_3$ and $CF_3CHFCF_3$; and perfluorocarbons such as $CF_3CF_3$ and $CF_3CF_2CF_3$.

Where mixtures of the fluorocarbons or hydrogen-containing chlorofluorocarbons are employed they may be mixtures of the above identified compounds, preferably binary mixtures, with other fluorocarbons or hydrogen-containing chlorofluorocarbons for example $CHClF_2$, $CH_2F_2$ and $CF_3CH_3$. Particularly preferred as propellants are $C_{1-4}$ hydrogen-containing fluorocarbons such as 1,1,1,2-tetrafluoroethane ($CF_3CH_2F$) and 1,1,1,2,3,3,3-heptafluoro-n-propane ($CF_3CHFCF_3$) or mixtures thereof. Preferably a single fluorocarbon or hydrogen-containing chlorofluorocarbon is employed as the propellant e.g. 1,1,1,2-tetrafluoroethane (HFA 134a) or 1,1,1,2,3,3,3-heptafluoro-n-propane (HFA 227), especially 1,1,1,2-tetrafluoroethane.

It is desirable that the formulations of the invention contain no components which may provoke the degradation of stratospheric ozone. In particular it is desirable that the formulations are substantially free of chlorofluorocarbons such as $CCl_3F$, $CCl_2F_2$ and $CF_3CCl_3$.

If desired the propellant may additionally contain a volatile adjuvant such as a saturated hydrocarbon for example propane, n-butane, isobutane, pentane and isopentane or a dialkyl ether, for example, dimethyl ether. In general, up to 50% w/w of the propellant may comprise a volatile hydrocarbon, for example 1 to 30% w/w. However, formulations which are substantially free of volatile adjuvants are preferred. In certain cases, it may be desirable to include appropriate amounts of water, which can be advantageous in modifying the dielectric properties of the propellant.

Polar adjuvants which may if desired, be incorporated into the formulations according to the present invention include e.g. $C_{2-6}$ aliphatic alcohols and polyols such as ethanol, isopropanol and propylene glycol and mixtures thereof. Preferably ethanol will be employed. In general only small quantities (e.g. 0.05 to 3.0% w/w) of polar adjuvants are required and the use of quantities in excess of 5% w/w may disadvantageously tend to dissolve the medicament. Formulations preferably contain less than 1% w/w, e.g. about 0.1% w/w of polar adjuvant. Polarity may be determined for example, by the method described in European Patent Application Publication No. 0327777.

However as the compounds of formula (I) are adequately soluble in the fluorocarbon or hydrogen-containing chlorofluorocarbon propellant the need to use a polar adjuvant is obviated. This is advantageous as polar adjuvants especially ethanol are not suitable for use with all patient groups. Formulations containing a compound of formula (I) which avoid use of a polar adjuvant are preferred.

In addition to one or more compounds of the general formula (I), the formulations according to the present invention may optionally contain one or more further ingredients conventionally used in the art of pharmaceutical aerosol formulation. Such optional ingredients include, but are not limited to, taste masking agents, sugars, buffers, antioxidants, water and chemical stabilisers.

A particularly preferred embodiment of the invention provides a pharmaceutical aerosol formulation consisting essentially of one or more particulate medicament(s), one or more fluorocarbon or hydrogen-containing chlorofluorocarbon propellant(s) and one or more compound(s) of formula (I).

A further embodiment of the invention is a sealed container capable of withstanding the pressure required to maintain the propellant as a liquid, such as a metered dose inhaler, containing therein the aerosol formulation as described above.

The term "metered dose inhaler" or MDI means a unit comprising a can, a secured cap covering the can and a formulation metering valve situated in the cap. MDI system includes a suitable channeling device. Suitable channeling devices comprise, for example, a valve actuator and a cylindrical or cone-like passage through which medicament may be delivered from the filled canister via the metering valve to the nose or mouth of a patient e.g. a mouthpiece actuator.

As an aspect of this invention there are also provided processes for the preparation of compounds of formula (I).

Therefore a process for preparing a compound of formula (I) is provided which comprises:

(a) preparation of a compound of formula (I) wherein $R^2$ represents the same as $R^3$, $R^4$ represents the same as $R^5$, $X^1$ represents the same as $X^2$, $Y^1$ and $Y^2$ represent carbonyl, m represents the same as n and p represents the same as q, by reacting a compound of formula (II)$^1$

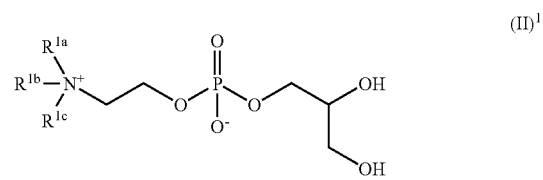

or a salt thereof, wherein $R^{1a}$, $R^{1b}$ and $R^{1c}$ are as defined above, with a compound of formula (III)$^1$

or an activated derivative thereof, wherein $R^2$, $R^4$, $X^1$, n and p are as defined above; or (b) preparation of a compound of formula (I) wherein $Y^1$ represents carbonyl which comprises reacting a compound of formula (IV)$^1$

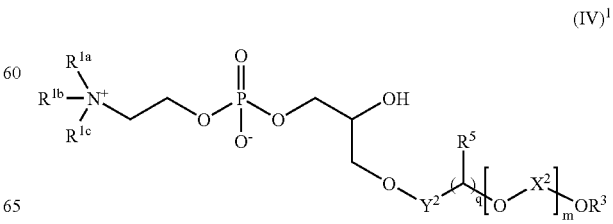

or a salt thereof, wherein $R^{1a}$, $R^{1b}$, $R^{1c}$, $R^3$, $R^5$, $X^2$, $Y^2$, m and q are as defined above, with a compound of formula (III)$^1$ or an activated derivative thereof; or (c) preparation of a compound of formula (I) wherein $Y^2$ represents carbonyl which comprises reacting a compound of formula (IV)$^2$ (IV)$^2$ or a salt thereof, wherein $R^{1a}$, $R^{1b}$, $R^{1c}$, $R^2$, $R^4$, $X^1$, $Y^1$ n and p are as defined above with a compound of formula (III)$^2$ (III)$^2$ or an activated derivative thereof, wherein $R^3$, $R^5$, $X^2$, m and q are as defined above; or (d) preparation of a compound of formula (I), wherein $R^2$ represents the same as $R^3$, $R^4$ represents the same as $R^5$, $X^1$ represents the same as $X^2$, $Y^1$ represents the same as $Y^2$, m represents the same as n, and p represents the same as q, by reacting a compound of formula (II)$^2$ (II)$^2$ wherein $R^{1a}$, $R^{1b}$, $R^{1c}$ are as defined above and $L^1$ and $L^2$ represent leaving groups with a compound of formula (V)$^1$ (V)$^1$ or a salt thereof, wherein $R^2$, $R^4$, $X^1$, $Y^1$, n and p are as defined above; or (e) reacting a compound of formula (VI)$^1$ (VI)$^1$ wherein $R^{1a}$, $R^{1b}$, $R^{1c}$, $R^3$, $R^5$, $X^2$, $Y^2$, m, q and $L^1$ are as defined above with a compound of formula (V)$^1$ or a salt thereof; or (f) reacting a compound of formula (VI)$^2$ (VI)$^2$ wherein $R^{1a}$, $R^{1b}$, $R^{1c}$, $R^2$, $R^4$, $X^1$, $Y^1$, n, p and $L^2$ are as defined above with a compound of formula (V)$^2$ (V)$^2$ or a salt thereof, wherein $R^3$, $R^5$, $X^2$, $Y^2$, m and q are as defined above; or (g) preparing a compound of formula (I), wherein $R^2$ represents the same as $R^3$, $X^1$ represents the same as $X^2$ and n represents the same as m, by reacting a compound of formula (VII)$^1$ (VII)$^1$ or a salt thereof, wherein $R^{1a}$, $R^{1b}$, $R^{1c}$, $R^4$, $R^5$, $Y^1$, $Y^2$, p and q are as defined above with a compound of formula (VIII)$^1$ (VIII)$^1$ wherein $R^2$, $X^1$ and n are as defined above and $L^3$ represents a leaving group; or (h) reacting a compound of formula (IX)$^1$ (IX)$^1$ or a salt thereof, wherein $R^{1a}$, $R^{1b}$, $R^{1c}$, $R^3$, $R^4$, $R^5$, $X^2$, $Y^1$, $Y^2$, m, p and q are as defined above with a compound of formula (VIII)$^1$; or (i) reacting a compound of formula (IX)$^2$

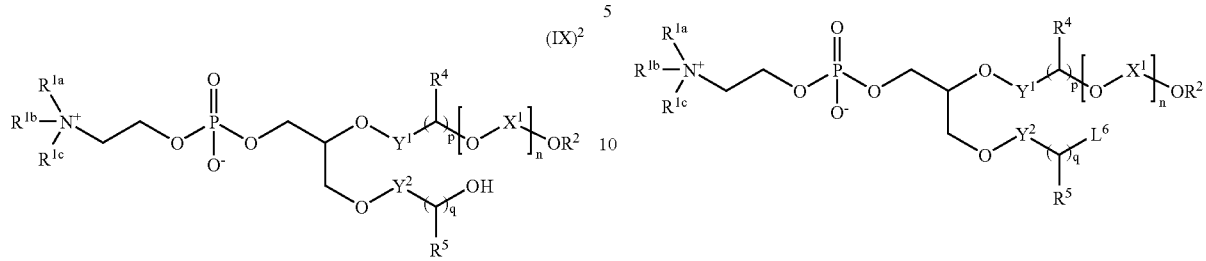

(IX)$^2$ or a salt thereof, wherein $R^{1a}$, $R^{1b}$, $R^{1c}$, $R^2$, $R^4$, $R^5$, $X^1$, $Y^1$, $Y^2$, n, p and q are as defined above with a compound of formula (VIII)$^2$

(VIII)$^2$ wherein $R^3$, $X^2$ and m are as defined above and $L^4$ represents a leaving group; or (j) preparing a compound of formula (I) wherein $R^2$ represents the same as $R^3$, $X^1$ represent the same as $X^2$ and n represents the same as m by reacting a compound of formula (VII)$^2$

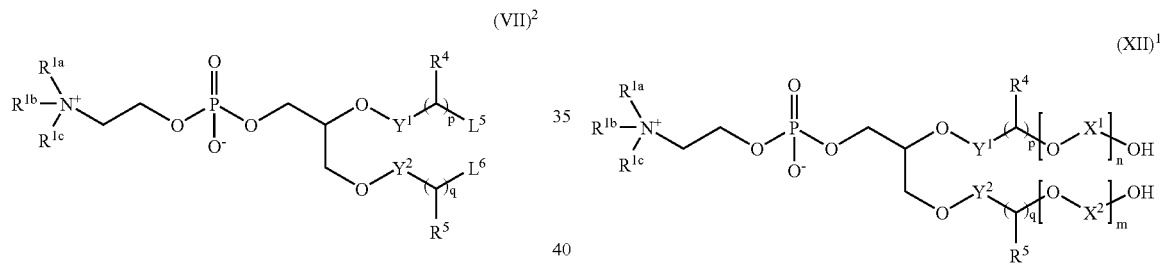

(VII)$^2$ wherein $R^{1a}$, $R^{1b}$, $R^{1c}$, $R^4$, $R^5$, $Y^1$, $Y^2$, p and q are as defined above and $L^5$ and $L^6$ represent leaving groups, with a compound of formula (X)$^1$

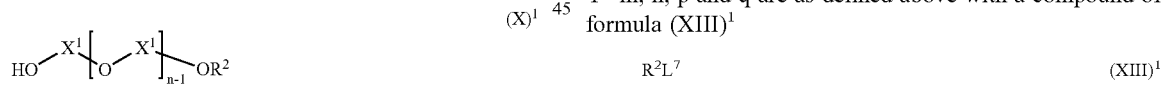

(X)$^1$ or a salt thereof, wherein $R^2$, $X^1$ and n are as defined above; or (k) reacting a compound of formula (XI)$^1$

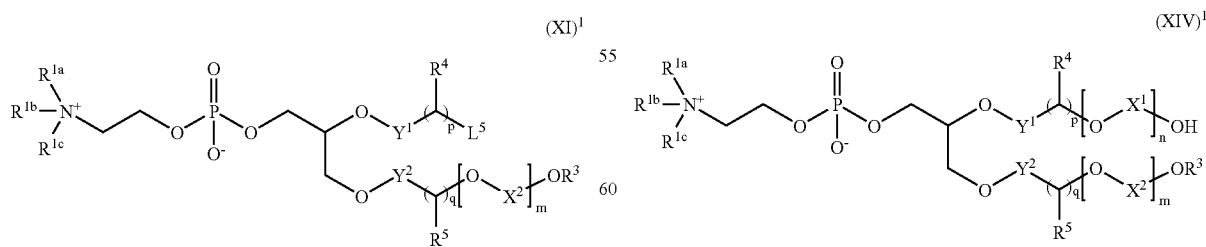

(XI)$^1$ wherein $R^{1a}$, $R^{1b}$, $R^{1c}$, $R^3$, $R^4$, $R^5$, $X^2$, m, p, q and $L^5$ are as defined above, with a compound of formula (X)$^1$ or a salt thereof; or (l) reacting a compound of formula (XI)$^2$

(XI)$^2$ wherein $R^{1a}$, $R^{1b}$, $R^{1c}$, $R^2$, $R^4$, $R^5$, $X^1$, $Y^1$, $Y^2$, n, p, q and $L^6$ are as defined above with a compound of formula (X)$^2$

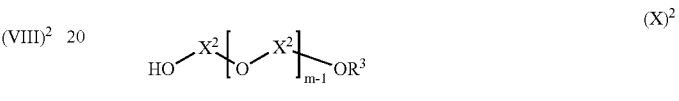

(X)$^2$ or a salt thereof, wherein $R^3$, $X^2$ and m are as defined above; or (m) preparing a compound of formula (I) wherein $R^2$ represent the same as $R^3$, by reacting a compound of formula (XII)$^1$

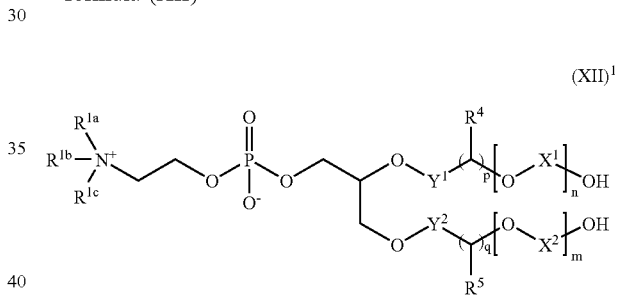

(XII)$^1$ or a salt thereof, wherein $R^{1a}$, $R^{1b}$, $R^{1c}$, $R^4$, $R^5$, $X^1$, $X^2$, $Y^1$, $Y^2$ m, n, p and q are as defined above with a compound of formula (XIII)$^1$ $R^2L^7$      (XIII)$^1$ wherein $R^2$ is as defined above and $L^7$ is a leaving group; or (n) reacting a compound of formula (XIV)$^1$

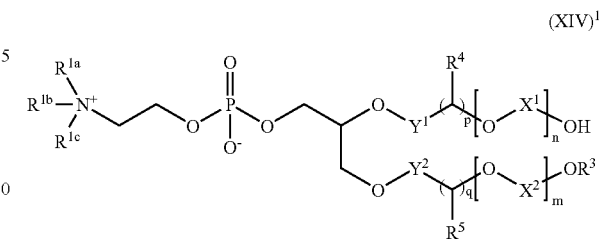

(XIV)$^1$ or a salt thereof, wherein $R^{1a}$, $R^{1b}$, $R^{1c}$, $R^3$, $R^4$, $R^5$, $X^1$, $X^2$, $Y^1$, $Y^2$, m, n, p and q are as defined above with a compound of formula (XIII)$^1$; or (o) reacting a compound of formula (XIV)²

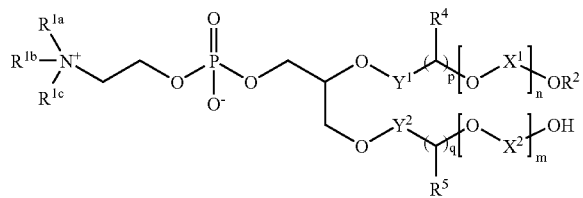
(XIV)² or a salt thereof, wherein $R^{1a}$, $R^{1b}$, $R^{1c}$, $R^2$, $R^4$, $R^5$, $X^1$, $X^2$, $Y^1$, $Y^2$, m, n, p and q are as defined above with a compound of formula (XIII)²

$$R^3L^8 \quad (XIII)^2$$

wherein $R^3$ is as defined above and $L^8$ represents a leaving group; or (p) preparing a compound of formula (I) wherein $R^2$ represent the same as $R^3$ by reacting a compound of formula (XII)²

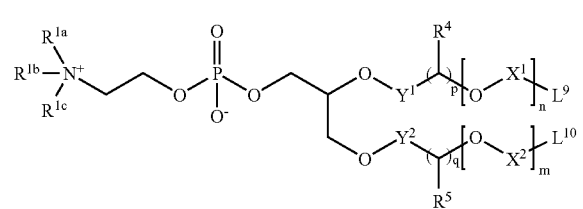
(XII)² wherein $R^{1a}$, $R^{1b}$, $R^{1c}$, $R^4$, $R^5$, $X^1$, $X^2$, $Y^1$, $Y^2$, m, n, p and q are as defined above and $L^9$ and $L^{10}$ represent leaving groups, with a compound of formula (XV)¹

$$R^2OH \quad (XV)^1$$

or a salt thereof, wherein $R^2$ is as defined above; or
(q) reacting a compound of formula (XVI)¹

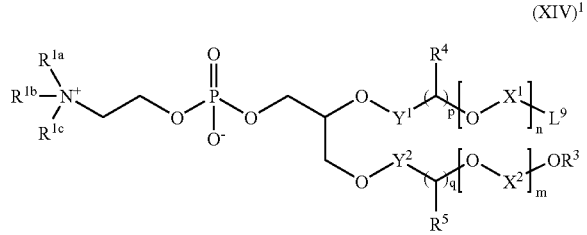
(XIV)¹ wherein $R^{1a}$, $R^{1b}$, $R^{1c}$, $R^3$, $R^4$, $R^5$, $X^1$, $X^2$, $Y^1$, $Y^2$, m, n, p, q and $L^9$ are as defined above, with a compound of formula (XV)¹ or a salt thereof; or
(r) reacting a compound of formula (XVI)²

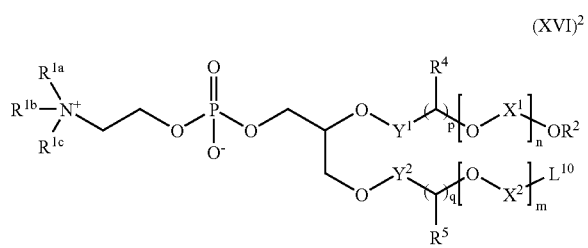
(XVI)² wherein $R^{1a}$, $R^{1b}$, $R^{1c}$, $R^2$, $R^4$, $R^5$, $X^1$, $X^2$, $Y^1$, $Y^2$, m, n, p, q and $L^{10}$ are as defined above, with a compound of formula (XV)²

$$R^3OH \quad (XV)^2$$

or a salt thereof, wherein $R^3$ is as defined above; or
(s) preparing a compound of formula (I) wherein $R^{1a}$ represents the same as $R^{1b}$ and $R^{1c}$ by reacting a compound of formula (XVII)

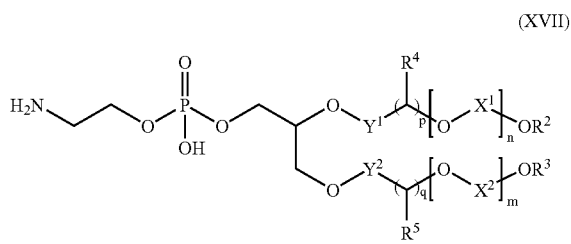
(XVII)

wherein $R^2$, $R^3$, $R^4$, $R^5$, $X^1$, $X^2$, $Y^1$, $Y^2$, m, n, p and q are as defined above with a compound of formula (XVIII)

$$R^{1a}L^{11} \quad (XVIII)$$

wherein $R^{1a}$ is as defined above and $L^{11}$ represents a leaving group; or (t) preparing a compound of formula (I) wherein $R^2$ and $R^3$ independently represent $C_{1-4}$ alkyl optionally substituted by up to 5 fluorine atoms, by reacting a compound of formula (XIX)

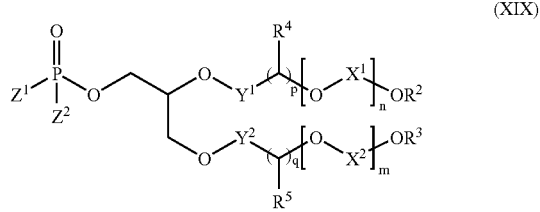
(XIX)

wherein $R^2$ and $R^3$ independently represent $C_{1-4}$ alkyl optionally substituted with up to 5 fluorine atoms and $R^4$, $R^5$, $X^1$, $X^2$, $Y^1$, $Y^2$, m, n, p and q are as defined above and $Z^1$ and $Z^2$ represent a halogen with a compound of formula (XX)

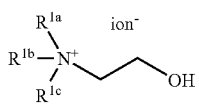
(XX)

wherein $R^{1a}$, $R^{1b}$ and $R^{1c}$ are as defined above and ion⁻ represents a negative counter ion (e.g. chloro) followed by aqueous work up; or (u) reacting a compound of formula (XXI)

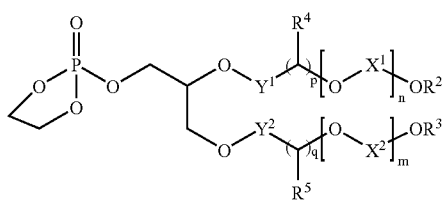

wherein $R^2$, $R^3$, $R^4$, $R^5$, $X^1$, $X^2$, $Y^1$, $Y^2$, m, n, p and q are as defined above wits a compound of formula (XXII)

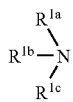

or a salt thereof, wherein $R^{1a}$, $R^{1b}$, and $R^{1c}$ are as defined above.

In process (a) above the reaction will usually take place under basic conditions e.g. in the presence of a non-nucleophilic base such as diisopropylamine in an inert solvent e.g. tetrahydrofuran (THF) at non-extreme temperatures e.g. 0-50° C. such as room temperature.

Conditions analogous to those described for process (a) are suitable for use in process (c) (d), (e), (f), (g), (h), (i) (j), (k), (l), (m), (n), (o), (p), (q), (r) and (s). Where the corresponding salt of the acid or alcohol (i.e. the alkoxide) is used this can be prepared by methods well known to persons skilled in the art e.g. the alkoxide can be prepared by reacting the alcohol with a hydride e.g. sodium hydride in the presence of an inert solvent. Suitable leaving groups for $L^1$, $L^2$, $L^3$, $L^4$, $L^5$, $L^6$, $L^7$, $L^8$, $L^9$, $L^{10}$ and $L^{11}$ including halogen e.g. bromo or chloro, —O-tosyl, —O-brosyl, —O-mesyl or —O-triflyl.

Where the compound of formula $(III)^1$ or $(III)^2$ used is an acid, the above reactions may be promoted by the presence of a coupling agent such as 1,3-dicyclohexylcarbodiimide (DCC) or 1,1-carbonyldiimidazole optionally in the presence of a solubilising agent such as 1,8-diazabicyclo[5.4.0]undec-7-ene (DBU) or 4-dimethylaminopyridine (DMAP). Preferably compounds of formula $(III)^1$ or $(III)^2$ will be used as an activated derivative.

Activated derivatives of compounds of formula $(III)^1$ and $(III)^2$ include acid halides e.g. acid chlorides and acid bromides; anhydrides including mixed anhydrides and activated esters.

Acid halides can be prepared from the corresponding acid using a halogenating agent e.g. thionyl chloride, oxalyl chloride, oxalyl bromide, phosphorus oxychloride or phosphorus oxybromide under standard conditions e.g. at non-extreme temperatures, for example, 0-75° C. such as room temperature. Inert solvents may be used, however often the reaction is performed without the addition of solvent.

Anhydrides generally can be prepared by reacting an acid with an acid halide in an inert solvent such as DCM or THF under basic conditions e.g. in the presence of a non-nulcleophilic base such as triethylamine at non-extreme temperatures e.g. 0-50° C. such as room temperature. A suitable reagent for use in the preparation of a mixed anhydride is trimethylacetyl chloride. The mixed anhydride formed using this reagent when taken on to the next stage of the reaction has the advantage that it provides some regioselectivity as attack of one carbonyl is hindered by the t-butyl substituent adjacent to it.

"Activated esters" are more reactive than simple esters as they contain a good leaving group. These may be formed e.g. in situ by stirring the corresponding acid in an inert solvent at a non-extreme temperature, e.g. room temperature, with for example 1-hydroxybenzotriazole (HOBT) or 1-hydroxy-7-azabenzotriazole (HOAT).

In process (t) the reaction will usually take place under basic conditions e.g. in the presence of a non-nucleophilic base such as pyrimidine, in an inert solvent such as trichloromethane, at a non-extreme temperature e.g. −10 to 50° C. such as 0 to 25° C. The further step of quenching the reaction with water is necessary to hydrolyse the phosphorus chloride bond and generate a compound of formula (I).

In process (u) the reaction will usually be performed in an inert solvent e.g. DCM, THF, DMF or acetonitrile, such as acetonitrile at a non-extreme temperature e.g. 0-100° C. such as 65° C., in a container capable of withstanding changes in pressure. Where the compound of formula (XXI) is a gas it may be cooled to a temperature in the range −10 to 20° C. such as 0° C. before it is introduced into the reaction mixture which is then heated in a pressure vessel.

Compounds of formula $(IV)^1$ may be prepared by:
(i) reacting a compound of formula $(II)^1$ or a protected derivative thereof with a compound of formula $(III)^2$; or
(ii) reacting a compound of formula (XXIII)

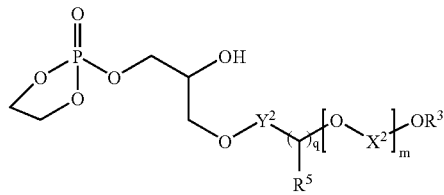

or a protected derivative thereof wherein the free alcohol is protected and $R^3$, $X^2$, $Y^2$, q and m are as defined above, with a compound of formula (XXII).

Process (i) may be performed under analogous conditions to those described above for process (a). Preferably the non-reacting hydroxyl will be protected.

Process (ii) may be performed under analogous conditions to those described above for process (t). Preferably the non-reacting hydroxyl will be protected.

Examples of protecting groups (e.g. for hydroxyl or amino) and means for their removal can be found in "Protecting Groups In Organic Synthesis" by Theodora Green and Peter G. M Wuts (John Wiley and Sons Inc 1999). Suitable hydroxylprotecting groups include but are not limited to carboxylic acid esters e.g. acetate ester, aryl esters e.g. benzoate ester, ethers e.g. benzyl ether and p-methoxybenzyl ether, tetrahydropyranyl ether and silyl ethers e.g. tert-butyldimethylsilyl ether. When some or all of $R^{1a}$, $R^{1b}$ and $R^{1c}$ represent hydrogen it may be necessary to protect the amine e.g. with carbobenzyloxy (CBZ), N-tert-butoxycarbonyl (BOC) or trifluoroacetyl (TFA).

Protecting groups can be removed by acid or base catalysed hydrolysis or reduction for example hydrogenation. Silyl ethers may require tetrabutylammonium fluoride or tetrabutylammonium fluoride to be cleaved. Where hydroxyl is protected as the benzyl ether, the protecting group may be removed, for example, by hydrogenation. Where hydroxyl is protected as the THP ether, the protecting group may be removed, for example, by acid hydrolysis. Wherein an amino group is protected by BOC or CBZ removal of the protecting group may be carried out, for instance by hydrogenation. Wherein an amino group is protected by TFA it can be removed by base hydrolysis, for example, sodium or potassium carbonate in methanol and water.

The following compounds may be prepared by analogous methods to those described for the preparation of compounds of formula $(IV)^1$ or (I) above: $(IV)^2$, $(VII)^1$, $(IX)^1$, $(IX)^2$, $(XII)^1$, $(XIV)^1$, $(XIV)^2$ and $(XVII)$.

Thus compounds of formula $(IV)^2$ can be prepared by reacting a compound of formula $(II)^1$ or a protected derivative thereof with a compound of formula $(III)^1$; compounds of formula $(VII)^1$ may be prepared by reacting compounds of formula $(II)^1$ with a compound of formula $(XXIV)^1$

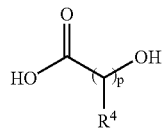

(XXIV)$^1$ or an activated derivative thereof and/or a protected derivative thereof wherein the free hydroxyl is protected $R^4$ and p are as defined above; compounds of formula $(IX)^1$ may be prepared by reacting a compound of formula $(IV)^1$ with a compound of formula $(XXIV)^1$; compounds of formula $(IX)^2$ may be prepared by reacting a compound of formula $(IV)^2$ with a compound of formula $(XXIV)^2$

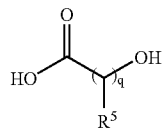

(XXIV)$^2$ or an activated derivative thereof and/or a protected derivative thereof wherein the free hydroxyl is protected wherein, $R^5$ and q are as defined above; compounds of formula $(XII)^1$ (wherein $X^1$ represents the same as $X^2$, $Y^1$ represents the same as $Y^2$, n represents the same as m and p represents the same as q) may be prepared by reacting compounds of formula $(II)^1$ with a compound of formula $(XXV)$

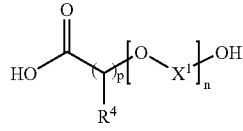

(XXV)

or an activated derivative thereof and/or a protected derivative thereof wherein the free hydroxyl is protected and wherein $R^4$, $X^1$, $Y^1$, n and p are as defined above. Other compounds of formula $(XII)^1$ can be prepared by methods analogous to those described herein; compounds of formula $(XIV)^1$ may be prepared by reacting a compound of formula $(XII)^1$ or a protected derivative thereof with a compound of formula $(XIII)^2$; compounds of formula $(XIV)^2$ may be prepared by reacting compounds of formula $(XII)^1$ or a protected derivative thereof with a compound of formula $(XIII)^1$; compounds of formula $(XVII)$ wherein $R^2$ represents the same as $R^3$ may be prepared by reacting a compound of formula $(XII)^1$ with a compound of formula $(XIII)^2$.

Compounds of formula $(II)^2$, $(VI)^1$, $(VI)^2$, $(VII)^2$, $(XI)^1$, $(XI)^2$, $(XII)^2$, $(XVI)^1$ and $(XVI)^2$ may be prepared from the corresponding alcohol for example:

i) wherein the leaving group is a halogen e.g. chloro or bromo the compounds may be prepared by reacting the corresponding alcohol with a halogenating agent under standard conditions; or ii) wherein the leaving group is selected from the list: —O-tosyl, —O-brosyl, —O-mesyl and —O-triflyl the compounds may be prepared by standard methods.

Suitable halogenating agents are described above.

Other leaving groups can be prepared as described in Advanced Organic Chemistry Reactions, Mechanisms and Structures (fourth edition) by Jerry March page 354 and 355. For example tosylates may be prepared by reacting the corresponding alcohol with para-toluene sulphonic acid.

Alternatively compounds of formula $(VII)^2$ wherein $L^5$ and $L^6$ represent halogen and $Y^1$ and $Y^2$ represent carbonyl may be prepared by:

(i) preparing a compound of formula $(VII)^2$ in which $R^4$ represents the same as $R^5$ and p represents the same as q by reacting a compound of formula $(II)^1$ as defined above with a compound of formula $(XXVI)$

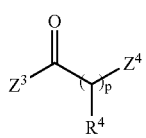

(XXVI)

wherein $Z^3$ and $Z^4$ independently represent a halogen, especially chlorine or bromine;

(ii) preparing a compound of formula $(VII)^2$ in which $R^4$ and $R^5$ represent hydrogen, p represents the same as q and $L^5$ and $L^6$ represent Br by reacting a compound of formula $(XXVII)$

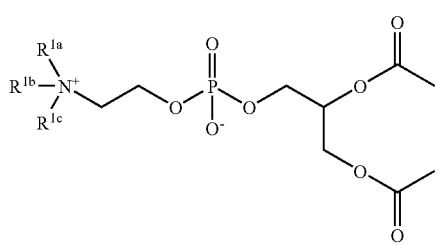

(XXVII)

wherein $R^{1a}$, $R^{1b}$ and $R^{1c}$ are as defined above, with $Br_2$.

Typical conditions for part (i) above would include performing the reaction under basic conditions optionally in an inert solvent at non-extreme temperatures e.g. 0-50° C. Process (ii) may be performed in under conditions analogous to those described for (i). Compounds of formula $(XIX)$ wherein $Z^1$ and $Z^2$ represent chlorine may be prepared by reacting a compound of formula (XXVIII)

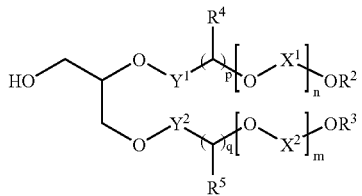
(XXVIII)

with $POCl_3$ in the presence of a base. Other compounds of formula (XIX) in which $Z^1$ and $Z^2$ represent a halogen other than chlorine may be prepared by analogous methods.

The reaction may be performed in an inert solvent e.g. an ether such as isopropyl ether at a non-extreme temperature e.g. −30 to 50° C. such as −25° C. to room temperature. In the presence of a non-nulceophilic base such as triethylamine.

Compounds of formula (XXI) may be prepared by reacting a compound of formula (XXVII) with a compound of formula (XXIX)

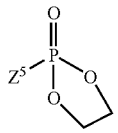
(XXIX)

wherein $Z^5$ represents a halogen, especially chlorine.

The reaction may be performed in an inert solvent such as toluene in the presence of a non-nucleophilic base such as triethylamine at a non-extreme temperature e.g. 0-50° C. such as room temperature.

Compounds of formula (XXIII) may be prepared by reacting a compound of formula (XXIX) with a compound of formula (XXX)

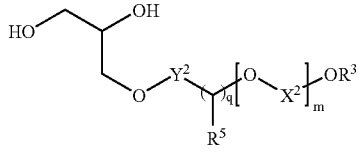
(XXX)

or a protected derivative thereof wherein the secondary alcohol is protected and wherein $R^3$, $R^5$, $X^2$, $Y^2$, m and q are as defined above.

Suitable conditions for this reaction are described above for the preparation of compounds of formula (XXI).

Compounds of formula (XXVII) may be prepared by reacting a compound of formula (II)$^1$ with an acetylating agent.

Compounds of formula (XXVIII) may be prepared by reacting glycerol with a compound of formula (III)$^1$ or an activated derivative thereof and/or (III)$^2$ or an activated derivative thereof and/or (VIII)$^1$ and/or (VIII)$^2$ as the case may be to obtain the desired combination. Wherein p represents the same as q, n represents the same as m, $R^2$ represents the same as $R^3$, $R^4$ represents the same as $R^5$ and $X^1$ represents the same as $X^2$ at least two molar equivalents of the compound of formula (III)$^1$ or (III)$^2$ (being the same compound) or (VIII)$^1$ or (VIII)$^2$ (being the same compound) will be used. For other compounds of formula (XXVIII) the reaction may be performed sequentially. Preferably the non-reacting hydroxyl(s) of the glycerol will be protected.

Compounds of formula (XXX) may be prepared from epibromohydrin with a compound of formula (V)$^2$ followed by a work up e.g. with water.

Compounds of formula (II)$^1$, (II)$^2$, (III)$^1$, (III)$^2$, (V)$^1$, (V)$^2$, (VIII)$^1$, (VIII)$^2$, (X)$^1$, (X)$^2$, (XIII)$^1$ (XIII)$^2$, (XV)$^1$, (XV)$^2$, (XVIII), (XX), (XXII), (XXIV)$^1$, (XXIV)$^2$, (XXV), (XXVI) and (XXIX) are either known or may be prepared by known methods.

Variations of the above methods which are common in the art are within the scope of this invention. It will be understood it may be necessary to use protecting groups in the preparation of the compounds of the invention. Examples of suitable protecting groups that may be employed include those recited above.

Compounds of formula (IV)$^1$, (IV)$^2$, (VI)$^1$, (VI)$^2$, (VII)$^1$, (VII)$^2$, (IX)$^1$, (IX)$^2$, (XI)$^1$, (XI)$^2$, (XII)$^1$, (XII)$^2$, (XIV)$^1$, (XIV)$^2$, (XVI)$^1$, (XVI)$^2$, (XVII), (XIX), (XXI), (XXIII), (XXVII) (XXVIII) and (XXX) are new and form an aspect of the invention.

In addition processes for preparing formulations including one or more compounds of formula (I) form an aspect of this invention.

The formulations of the invention may be prepared by dispersal of the medicament and a compound of formula (I) in the selected propellant in an appropriate container, e.g. with the aid of sonication or a high-shear mixer. The process is desirably carried out under controlled humidity conditions.

The chemical and physical stability and the pharmaceutical acceptability of the aerosol formulations according to the invention may be determined by techniques well known to those skilled in the art. Thus, for example, the chemical stability of the components may be determined by HPLC assay, for example, after prolonged storage of the product. Physical stability data may be gained from other conventional analytical techniques such as, for example, by leak testing, by valve delivery assay (average shot weights per actuation), by dose reproducibility assay (active ingredient per actuation) and spray distribution analysis.

The suspension stability of the aerosol formulations according to the invention may be measured by conventional techniques, for example by measuring flocculation size distribution using a back light scattering instrument or by measuring particle size distribution by cascade impaction or by the "twin impinger" analytical process. As used herein reference to the "twin impinger" assay means "Determination of the deposition of the emitted dose in pressurised inhalations using apparatus A" as defined in British Pharmacopaeia 1988, pages A204-207, Appendix XVII C. Such techniques enable the "respirable fraction" of the aerosol formulations to be calculated. One method used to calculate the "respirable fraction" is by reference to "fine particle fraction" which is the amount of active ingredient collected in the lower impingement chamber per actuation expressed as a percentage of the total amount of active ingredient delivered per actuation using the twin impinger method described above.

MDI canisters generally comprise a container capable of withstanding the vapour pressure of the propellant used such as a plastic or plastic-coated glass bottle or preferably a metal can, for example an aluminium or an alloy thereof which may optionally be anodised, lacquer-coated and/or plastic-coated (e.g. incorporated herein by reference WO96/32099 wherein part or all of the internal surfaces are coated with one or more fluorocarbon polymers optionally in combination with one or more non-fluorocarbon polymers), which container is closed with a metering valve. The cap may be secured onto the can via ultrasonic welding, screw fitting or crimping. MDIs taught herein may be prepared by methods of the art (e.g. see Byron, above and WO/96/32099). Preferably the canister is fitted with a cap assembly, wherein a formulation metering valve is situated in the cap, and said cap is crimped in place.

The metering valves are designed to deliver a metered amount of the formulation per actuation and incorporate a gasket to prevent leakage of propellant through the valve. The gasket may comprise any suitable elastomeric material such as for example low density polyethylene, chlorobutyl, black and white butadiene-acrylonitrile rubbers, butyl rubber and neoprene. Suitable valves are commercially available from manufacturers well known in the aerosol industry, for example, from Valois, France (e.g. DF10, DF30, DF60), Bespak plc, UK (e.g. BK300, BK357) and 3M-Neotechnic Ltd, UK (e.g. Spraymiser™).

A further aspect of this invention comprises a process for filling the said formulation into MDIs.

Conventional bulk manufacturing methods and machinery well known to those skilled in the art of pharmaceutical aerosol manufacture may be employed for the preparation of large scale batches for the commercial production of filled canisters. Thus, for example, in one bulk manufacturing method a metering valve is crimped onto an aluminium can to form an empty canister. The particulate medicament is added to a charge vessel and liquefied propellant is pressure filled through the charge vessel into a manufacturing vessel, together with liquefied propellant containing the surfactant. The drug suspension is mixed before recirculation to a filling machine and an aliquot of the drug suspension is then filled through the metering valve into the canister.

In an alternative process, an aliquot of the liquefied formulation is added to an open canister under conditions which are sufficiently cold to ensure the formulation does not vaporise, and then a metering valve crimped onto the canister.

Typically, in batches prepared for pharmaceutical use, each filled canister is check-weighed, coded with a batch number and packed into a tray for storage before release testing.

Each filled canister is conveniently fitted into a suitable channeling device prior to use to form a metered dose inhaler system for administration of the medicament into the lungs or nasal cavity of a patient. Metered dose inhalers are designed to deliver a fixed unit dosage of medicament per actuation or "puff", for example in the range of 10 to 5000 micrograms of medicament per puff.

Administration of medicament may be indicated for the treatment of mild, moderate, severe acute or chronic symptoms or for prophylactic treatment. It will be appreciated that the precise dose administered will depend on the age and condition of the patient, the particular particulate medicament used and the frequency of administration and will ultimately be at the discretion of the attendant physician. When combinations of medicaments are employed the dose of each component of the combination will in general be that employed for each component when used alone. Typically, administration may be one or more times, for example from 1 to 8 times per day, giving for example 1, 2, 3 or 4 puffs each time.

Suitable daily doses, may be, for example in the range 50 to 200 micrograms of salmeterol, 100 to 1000 micrograms of albuterol, 50 to 2000 micrograms of fluticasone propionate or 100 to 2000 micrograms of beclomethasone dipropionate, depending on the severity of the disease.

Thus, for example, each valve actuation may deliver 25 microgram salmeterol, 100 microgram albuterol, 25, 50, 125 or 250 microgram fluticasone propionate or 50, 100, 200 or 250 microgram beclomethasone dipropionate. Doses for Seretide™, which is a combination of salmeterol and fluticasone propionate, will usually be those given for the corresponding individual component drugs. Typically each filled canister for use in a metered dose inhaler system contains 60, 100, 120, 160 or 240 metered doses or puffs of medicament.

An appropriate dosing regime for other medicaments will be know or readily available to persons skilled in the art.

The use of the compounds of formula (I) as described above especially in the preparation of a pharmaceutical formulation; use of a formulation as described above in inhalation therapy e.g. for the treatment or prophylaxis of respiratory disorders; and use of a metered dose inhaler system in the treatment or prophylaxis of respiratory disorders are all alternative aspects of this invention.

A still further aspect of the present invention comprises a method of treating respiratory disorders such as, for example, asthma, which comprises administration by inhalation of an effective amount of a formulation as herein described.

The invention also includes use of compounds of formula (I) as a surfactant.

The following non-limiting examples serve to illustrate the invention.

EXAMPLES

Throughout the examples, the following abbreviations are used:
LCMS: Liquid Chromatography Mass Spectrometry.
RT: retention time
THF: tetrahydofuran
bp: boiling point
ca: circa
h: hour(s)
min: minute(s)

All temperatures are given in degrees Celsius.
Silica gel refers to Merck silica gel 60 Art number 7734.
Flash silica gel refers to Merck silica gel 60 Art number 9385.
Biotage™ refers to prepacked silica gel cartridges containing KP-Sil run on flash 12i chromatography module.
Bond Elut™ (C18 cartridge) are prepacked cartridges used in parallel purifications, normally under vacuum. These are commercially available from Varian.

Where organic solutions were dried during work up magnesium sulphate was used. LCMS was conducted on a Supelcosil LCABZ+PLUS column (3.3 cm×4.6 mm ID) eluting with 0.1% $HCO_2H$ and 0.01 M ammonium acetate in water (solvent A), and 0.05% $HCO_2H$ 5% water in acetonitrile (solvent B), using the following elution gradient 0-0.7 min 0% B, 0.7-4.2 min 100% B, 4.2-5.3 min 0% B, 5.3-5.5 min 0% B at a flow rate of 3 ml/min. High molecular weight LCMS was conducted on a Micromass LCTOF Time of Flight Mass spectrometer using electrospray positive mode. LCMS conditions are as described above.

Example 1

Bis(2,5,8,11,14,17,20-heptaoxadocosan-22-oyl)propyl-2-trimethylammonium ethyl phosphate

(a) Ethyl 2,5,8,11,14,17,20-heptaoxadocosan-22-oate

To a stirred solution of 2,5,8,11,14,17-hexanoxanonadecan-19-ol (5 g) in toluene (190 ml) was added potassium t-butoxide (2.66 g) and the reaction was stirred at room temperature for 2 hours. Ethyl bromoacetate (5.65 g) was added and the reaction stirred at 130° C. for 20 hours. The solvent was removed in vacuo and the residue partitioned between dichloromethane (750 ml) and water (750 ml). The organic layer was washed with brine (500 ml), dried and the solvent removed in vacuo. The residue was purified by column chromatography on silica gel (Biotage), eluting with 2% methanol in dichloromethane to give the title compound as a brown oil (4.54 g).

Retention time 2.27 mins Mass spectrum m/z 400 [MNH$_4^+$]

(b) 2,5,8,11,14,17,20-Heptaoxadocosan-22-oic acid

The product of step (a) (4.54 g) was dissolved in an aqueous sodium hydroxide solution (0.1M) (45 ml) and the reaction was stirred at room temperature for 20 hours. The reaction mixture was acidified to pH 2 by the addition of hydrochloric acid (2M), then this was diluted with brine (300 ml) and extracted with dichloromethane (3×300 ml). The combined organic layers were dried and the solvent removed in vacuo to give the title compound as a yellow oil (3.75 g).

Retention time 2.01 mins Mass spectrum m/z 372 [MNH$_4^+$]

(c) Bis(2,5,8,11,14,17,20-heptaoxadocosan-22-oyl)propyl-2-trimethylammonium ethyl phosphate To a stirred solution of the product of step (b) (250 mg) in tetrahydrofuran (15 ml) was added 4-dimethylaminopyridine (34 mg), triethylamine (113 mg) and pivaloyl chloride (102 mg). The reaction was stirred at room temperature for 30 minutes. Glycerophosphorylcholine (72 mg) was added and the reaction was stirred at 80° C. for 16 hours. The reaction mixture was filtered and the filtrate was concentrated in vacuo. The residue was purified by column chromatography on a C$_{18}$ cartridge (Bond Elut™) eluting with 10-20% acetonitrile in water to give the title compound as a yellow gum.

Retention time 2.20 mins Mass spectrum m/z 930 [MH$^+$]

Example 2

Bis(23,23,23-trifluoro-3,6,9,12,15,18,21-heptaoxatricosan-1-oyl)propyl-2-trimethylammonium ethyl phosphate

(a) 1-Phenyl-2,5,8,11,14,17-hexaoxanonadecan-19-ol

To a stirred suspension of sodium hydride (50% dispersion in mineral oil, 2.55 g) in tetrahydrofuran (100 ml) was added hexaethylene glycol (25 g). The reaction mixture was stirred at 5-15° C. for 10 minutes, then benzyl bromide (16.66 g) was added. The suspension was allowed to stand at 20° C. for 72 hours then the reaction mixture was diluted with water (250 ml) and extracted with cyclohexane (250+ 125 ml). 15% w/w. Aqueous sodium chloride solution (300 ml) was added to the aqueous phase and the resulting solution was extracted with ethyl acetate (3×250 ml). The combined ethyl acetate extracts were concentrated in vacuo to give the title compound as an orange oil (18.68 g).

Retention time 2.50 mins Mass spectrum m/z 390 [MNH$_4^+$]

(b) 19-Phenyl-3,6,9,12,15,18-hexaoxanonadec-1-yl 4-methylbenzenesulfonate

To a stirred solution of the product of step (a) (1 g) in dichloromethane (20 ml), p-toluenesulfonyl chloride (0.66 g) and triethylamine (0.5 ml) were added and the reaction was stirred at 20° C. for 24 hours. The reaction mixture was diluted with dichloromethane (100 ml) and washed with water (100 ml), brine (100 ml), dried and the solvent removed in vacuo. Purification by column chromatography on silica gel (Biotage) eluting with 10% ethyl acetate in cyclohexane gave the title compound (1 g).

Retention time 3.37 mins Mass spectrum m/z 544 [MNH$_4^+$]

(c) 22,22,22-Trifluoro-1-phenyl-2,5,8,11,14,17,20-heptaoxadocosane

To a stirred solution of trifluoroethanol (0.1 g) and sodium hydride (60% dispersion in mineral oil; (0.05 g) in tetrahydrofuran (10 ml) was added the product of step (b) (0.5 g) and the reaction stirred for 24 hours at 20° C. The reaction was quenched by the addition of methanol (5 ml) and the solvent removed in vacuo. The residue was partitioned between ethyl acetate (50 ml) and water (50 ml). The organic layer was washed with brine (50 ml), dried and the solvent removed in vacuo. Purification by column chromatography on silica gel (Biotage), eluting with 50% ethyl acetate in cyclohexane gave the title compound (0.27 g).

Retention time 3.17 mins Mass spectrum m/z 472 [MNH$_4^+$]

(d) 20,20,20-Trifluoro-3,6,9,12,15,18-hexaoxaicosan-1-ol

A stirred solution of the product of step (c) (16 g) and 10% palladium on carbon (1 g) in 1:1 acetic acid:ethanol (150 ml) was placed under an atmosphere of hydrogen at 20° C. for 24 hours. The reaction mixture was filtered through a pad of celite and the solvent removed in vacuo to give the title compound (11 g).

Mass spectrum m/z 382 [MNH$_4^+$]

(e) Ethyl 23,23,23-trifluoro-3,6,9,12,15,18,21-heptaoxatricosan-1-oate

To a stirred solution of the product of step (d) (1.5 g) in toluene (30 ml) was added potassium t-butoxide (0.69 g) and the reaction stirred at room temperature for 3 hours. Ethyl bromoacetate (1.38 g) was added and the reaction was stirred at 130° C. for 48 hours. The solvent was removed in vacuo and the residue dissolved in dichloromethane (500 ml) and washed with water (2×400 ml). The organic layer was washed with brine (300 ml), dried and the solvent removed in vacuo. The residue was purified by column chromatography on silica gel (Biotage), eluting with 65-75% ethyl acetate in cyclohexane to give the title compound as a brown oil (0.40 g).

Retention time 2.77 mins Mass spectrum IT/z 468 [$MNH_4^+$]

(f) 23,23,23-Trifluoro-3,6,9,12,15,18,21-heptaoxatricosan-1-oic acid

The product of step (e) (400 mg) was dissolved in an aqueous sodium hydroxide solution (0.1M) (10 ml) and the reaction was stirred at room temperature for 16 hours. The reaction mixture was acidified to pH 2 by the addition of hydrochloric acid (2M), then this was diluted with brine (200 ml) and extracted with dichloromethane (2×200 ml). The combined organic layers were dried and the solvent removed in vacuo to give the title compound as a colourless oil (330 mg).

Retention time 2.41 mins Mass spectrum m/z 440 [$MNH_4^+$]

(g) Bis(23,23,23-trifluoro-3,6,9,12,15,18,21-heptaoxatricosan-1-oyl)propyl-2-trimethylammonium ethyl phosphate To a stirred solution of the product of step (f) (220 mg) in tetrahydrofuran (15 ml) was added 4-dimethylaminopyridine (29 mg), triethylamine (97 mg) and pivaloyl chloride (87 mg). The reaction was stirred at room temperature for 5 minutes. Glycerophosphorylcholine (62 mg) was added and the reaction was stirred at 80° C. for 16 hours. The reaction mixture was filtered and the filtrate was concentrated in vacuo. The residue was purified by column chromatography on a $C_{18}$ cartridge (Bond Elut™) eluting with 10-30% acetonitrile in water to give the title compound as a colourless gum (60 mg).

Retention time 2.74 mins Mass spectrum m/z 1066 [$MH^+$]

The invention claimed is:

1. A compound of formula (I)

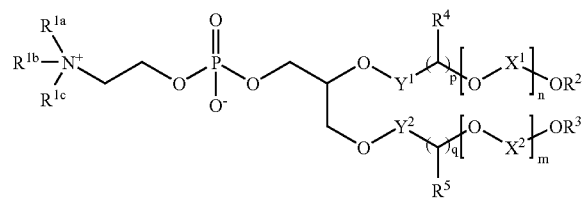

or a salt or solvate thereof wherein:
m, n, p and q independently represent an integer 1 to 12;
$R^{1a}$, $R^{1b}$ and $R^{1c}$ independently represent $C_{1-3}$ alkyl or hydrogen;
$R^2$ and $R^3$ independently represent $C_{1-4}$ alkyl optionally substituted with up to 5 fluorine atoms or —$COC_{1-2}$ alkyl optionally substituted with up to 5 fluorine atoms;
$R^4$ and $R^5$ independently represent —$CH_3$ or hydrogen;
$X^1$ and $X^2$ independently represent —$(CH_2)_2$—, —$(CH_2)_3$—, —$CH(CH_3)CH_2$—, —$CH_2CH(CH_3)$—, —$CH(CH_3)CH_2CH_2$—, —$CH_2CH(CH_3)CH_2$—, —$CH_2CH_2CH(CH_3)$— or —$COCH(CH_3)$—; and
$Y^1$ and $Y^2$ independently represent —$CH_2$— or carbonyl;
with the proviso that when:
p and q represent 1;
m and n independently represent an integer between 1 to 12;

$R^4$ and $R^5$ represent hydrogen;
$X^1$ and $X^2$ represent —$(CH_2)_2$—; and
$Y^1$ and $Y^2$ represent —$CH_2$—; then
$R^2$ and $R^3$ may only represent —$C_{1-2}$ alkyl optionally substituted with up to 5 fluorine atoms or —$COC_{1-2}$ alkyl optionally substituted with up to 5 fluorine atoms.

2. A compound according to claim 1, wherein n and m represent an integer 2 to 8.

3. A compound according to claim 1, wherein p and q represent an integer 1 to 6.

4. A compound according to claim 1, wherein $R^{1a}$ represents methyl.

5. A compound according to claim 1, wherein $R^{1b}$ represents methyl.

6. A compound according to claim 1, wherein $R^{1c}$ represents methyl.

7. A compound according to claim 1, wherein $R^4$ and $R^5$ represent hydrogen.

8. A compound according to claim 1, wherein $Y^1$ represents carbonyl.

9. A compound according to claim 1, wherein $Y^2$ represents carbonyl.

10. A compound according to claim 1, wherein
p and q independently represent 1 to 3;
$R^2$ and $R^3$ independently represent $C_{1-4}$ alkyl optionally substituted with up to 5 fluorine atoms or —$COC_{1-2}$ alkyl optionally substituted with up to 5 fluorine atoms;
$R^4$ and $R^5$ independently represent hydrogen or —$CH_3$;
$X^1$ and $X^2$ represent —$COCH(CH_3)$—; and
$Y^1$ and $Y^2$ represent carbonyl.

11. A compound according to claim 1, wherein
p and q independently represent 1 to 3;
$R^2$ and $R^3$ independently represent $C_{1-4}$ alkyl optionally substituted with up to 5 fluorine atoms or —$COC_{1-2}$ alkyl optionally substituted with up to 5 fluorine atoms;
$R^4$ and $R^5$ independently represent hydrogen or methyl;
$X^1$ and $X^2$ preferably independently represent —$(CH_2)_2$—, —$(CH_2)_3$—, —$CH(CH_3)CH_2$—, —$CH_2CH(CH_3)$—, —$CH(CH_3)CH_2CH_2$—, —$CH_2CH(CH_3)CH_2$— or —$CH_2CH_{2CH(CH_3)}$—; and
$Y^1$ and $Y^2$ independently represent —$CH_2$— or carbonyl.

12. A pharmaceutical aerosol formulation which comprises a particulate medicament, a fluorocarbon or hydrogen-containing chlorofluorocarbon propellant, or mixtures thereof, and a compound according to claim 1.

13. A pharmaceutical aerosol formulation according to claim 12 wherein the formulation contains 0.5% to 10% w/w of the compound according to claim 1, relative to the amount of the medicament.

14. A pharmaceutical aerosol formulation according to claim 12 wherein the formulation contains 0.01 to 1.0% w/w of medicament, relative to the total weight of the formulation.

15. A pharmaceutical aerosol formulation according to claim 12, wherein the propellant is 1,1,1,1,3,3,3-heptafluoro-n-propane or 1,1,1,2-tetrafluoroethane.

16. A metered dose inhaler comprising a formulation according to claim 12.

17. A process for preparing a compound of formula (I)

(I)

[chemical structure]

or a salt or solvate thereof wherein:
  m, n, p and q independently represent an integer 1 to 12;
  $R^{1a}$, $R^{1b}$ and $R^{1c}$ independently represent $C_{1-3}$ alkyl or hydrogen;
  $R^2$ and $R^3$ independently represent $C_{1-4}$ alkyl optionally substituted with up to 5 fluorine atoms or —$COC_{1-2}$ alkyl optionally substituted with up to 5 fluorine atoms;
  $R^4$ and $R^5$ independently represent —$CH_3$ or hydrogen;
  $X^1$ and $X^2$ independently represent —$(CH_2)_2$—, —$(CH_2)_3$—, —$CH(CH_3)CH_2$—, —$CH_2CH(CH_3)$—, —$CH(CH_3)CH_2CH_2$—, —$CH_2CH(CH_3)CH_2$—, —$CH_2CH_2CH(CH_3)$— or —$COCH(CH_3)$—; and
  $Y^1$ and $Y^2$ independently represent —$CH_2$— or carbonyl;
with the proviso that when:
  p and q represent 1;
  m and n independently represent an integer between 1 to 12;
  $R^4$ and $R^5$ represent hydrogen;
  $X^1$ and $X^2$ represent —$(CH_2)_2$—; and
  $Y^1$ and $Y^2$ represent —$CH_2$—; then
  $R^2$ and $R^3$ may only represent —$C_{1-2}$ alkyl optionally substituted with up to 5 fluorine atoms or —$COC_{1-2}$ alkyl optionally substituted with up to 5 fluorine atoms
said process comprising:
  (a) preparation of a compound of formula (I) wherein $R^2$ represents the same as $R^3$, $R^4$ represents the same as $R^5$, $X^1$ represents the same as $X^2$, $Y^1$ and $Y^2$ represent carbonyl, m represents the same as n, and p represents the same as q, by reacting a compound of formula (II)$^1$ (II)$^1$

[chemical structure]

or a salt thereof, wherein $R^{1a}$, $R^{1b}$ and $R^{1c}$ are as defined above for formula (I), with a compound of formula (III)$^1$ (III)$^1$

[chemical structure]

or an activated derivative thereof, wherein $R^2$, $R^4$, $X^1$, n and p are as defined above for formula (I); or (b) preparation of a compound of formula (I) wherein $Y^1$ represents carbonyl which comprises reacting a compound of formula (IV)$^1$ (IV)$^1$

[chemical structure]

or a salt thereof, wherein $R^{1a}$, $R^{1b}$, $R^{1c}$, $R^3$, $R^5$, $X^2$, $Y^2$, m and q are as defined above for formula (I), with a compound of formula (III)$^1$ or an activated derivative thereof; or (c) preparation of a compound of formula (I) wherein $Y^2$ represents carbonyl which comprises reacting a compound of formula (IV)$^2$ (IV)$^2$

[chemical structure]

or a salt thereof, wherein $R^{1a}$, $R^{1b}$, $R^{1c}$, $R^2$, $R^4$, $X^1$, $Y^1$ n and p are as defined above for formula (I) with a compound of formula (III)$^2$ (III)$^2$

[chemical structure]

or an activated derivative thereof, wherein $R^3$, $R^5$, $X^2$, m and q are as defined above for formula (I); or (d) preparation of a compound of formula (I), wherein $R^2$ represents the same as $R^3$, $R^4$ represents the same as $R^5$, $X^1$ represents the same as $X^2$, $Y^1$ represents the same as $Y^2$, m represents the same as n, and p represents the same as q, by reacting a compound of formula (II)$^2$ (II)$^2$

[chemical structure]

wherein $R^{1a}$, $R^{1b}$, $R^{1c}$ are as defined above for formula (I) and $L^1$ and $L^2$ represent leaving groups with a compound of formula (V)$^1$

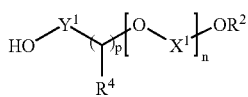

or a salt thereof, wherein $R^2$, $R^4$, $X^1$, $Y^1$, n and p are as defined above for formula (I); or (e) reacting a compound of formula (VI)$^1$

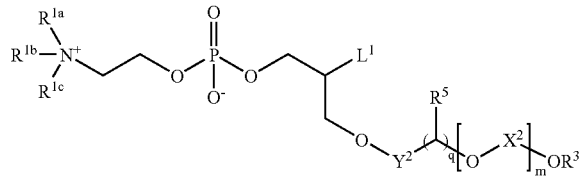

wherein $R^{1a}$, $R^{1b}$, $R^{1c}$, $R^3$, $R^5$, $X^2$, $Y^2$, m, q and $L^1$ are as defined above for formula (I) with a compound of formula (V)$^1$ or a salt thereof; or (f) reacting a compound of formula (VI)$^2$

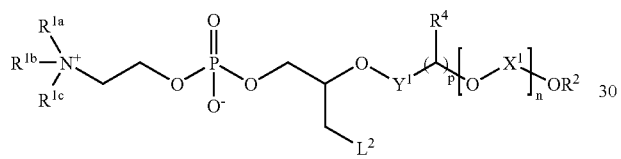

wherein $R^{1a}$, $R^{1b}$, $R^{1c}$, $R^2$, $R^4$, $X^1$, $Y^1$, n, p and $L^2$ are as defined above for formula (I) with a compound of formula (V)$^2$

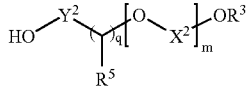

or a salt thereof, wherein $R^3$, $R^5$, $X^2$, $Y^2$, m and q are as defined above for formula (I); or (g) preparing a compound of formula (I), wherein $R^2$ represents the same as $R^3$, $X^1$ represents the same as $X^2$ and n represents the same as m, by reacting a compound of formula (VII)$^1$

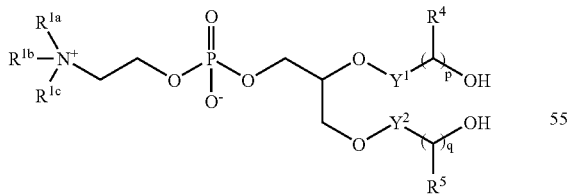

or a salt thereof, wherein $R^{1a}$, $R^{1b}$, $R^{1c}$, $R^4$, $R^5$, $Y^1$, $Y^2$, p and q are as defined

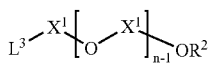

above for formula (I) with a compound of formula (VIII)$^1$ wherein $R^2$, $X^1$ and n are as defined above for formula (I) and $L^3$ represents a leaving group; or (h) reacting a compound of formula (IX)$^1$

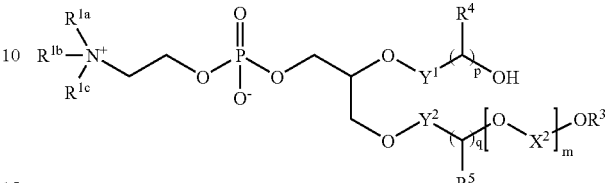

or a salt thereof, wherein $R^{1a}$, $R^{1b}$, $R^{1c}$, $R^3$, $R^4$, $R^5$ $X^2$, $Y^1$, $Y^2$, m, p and q are as defined above for formula (I) with a compound of formula (VIII)$^1$; or (i) reacting a compound of formula (IX)$^2$

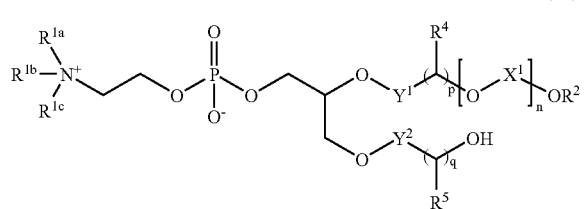

or a salt thereof, wherein $R^{1a}$, $R^{1b}$, $R^{1c}$, $R^2$, $R^4$, $R^5$, $X^1$, $Y^1$, $Y^2$, n, p and q are as defined above for formula (I) with a compound of formula (VIII)$^2$

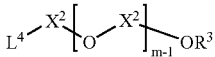

wherein $R^3$, $X^2$ and m are as defined above for formula (I) and $L^4$ represents a leaving group; or (j) preparing a compound of formula (I) wherein $R^2$ represents the same as $R^3$, $X^1$ represent the same as $X^2$ and n represents the same as m by reacting a compound of formula (VII)$^2$

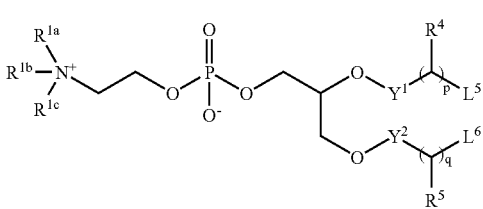

wherein $R^{1a}$, $R^{1b}$, $R^{1c}$, $R^4$, $R^5$, $Y^1$, $Y^2$, p and q are as defined above for formula (I) and $L^5$ and $L^6$ represent leaving groups, with a compound of formula (X)$^1$

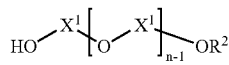

or a salt thereof, wherein $R^2$, $X^1$ and n are defined above for formula (I); or (k) reacting a compound of formula $(XI)^1$

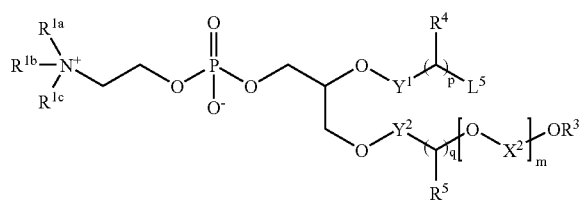

wherein $R^{1a}$, $R^{1b}$, $R^{1c}$, $R^3$, $R^5$, $X^2$, m, p, q and $L^5$ are as defined above for formula (I) with a compound of formula $(X)^1$ or a salt thereof; or (l) reacting a compound of formula $(XI)^2$

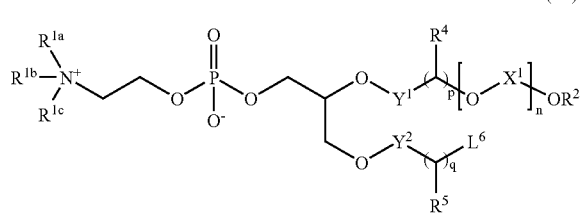

wherein $R^{1a}$, $R^{1b}$, $R^{1c}$, $R^2$, $R^4$, $R^5$, $X^1$, $Y^1$, $Y^2$, n, p, q and $L^6$ are as defined above for formula (I) with a compound of formula $(X)^2$

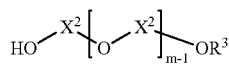

or a salt thereof, wherein $R^3$, $X^2$ and m are as defined above for formula (I); or (m) preparing a compound of formula (I) wherein $R^2$ represent the same as $R^3$, by reacting a compound of formula $(XII)^1$

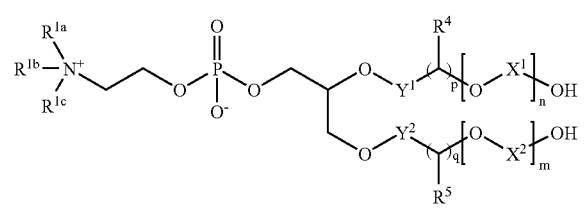

or a salt thereof, wherein $R^{1a}$, $R^{1b}$, $R^{1c}$, $R^4$, $R^5$, $X^1$, $X^2$, $Y^1$, $Y^2$, m, n, p and q are as defined above for formula (I) with a compound of formula $(XIII)^1$ $$R^2L^7 \qquad (XIII)^1$$

wherein $R^2$ is as defined above for formula (I) and $L^7$ is a leaving group; or (n) reacting a compound of formula $(XIV)^1$

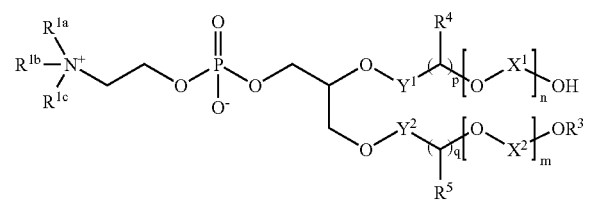

or a salt thereof, wherein $R^{1a}$, $R^{1b}$, $R^{1c}$, $R^3$, $R^4$, $R^5$, $X^1$, $X^2$, $Y^1$, $Y^2$, m, n, p and q are as defined above for formula (I) with a compound of formula $(XIII)^1$; or (o) reacting a compound of formula $(XIV)^2$

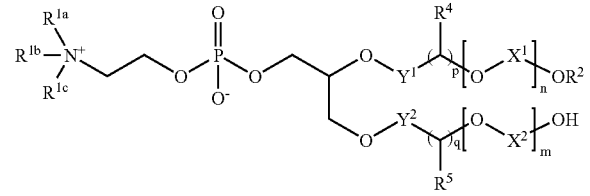

or a salt thereof, wherein $R^{1a}$, $R^{1b}$, $R^{1c}$, $R^2$, $R^4$, $R^5$, $X^1$, $X^2$, $Y^1$, $Y^2$, m, n, p and q are as defined above for formula (I) with a compound of formula $(XIII)^2$ $$R^3L^8 \qquad (XIII)^2$$

wherein $R^3$ is as defined above for formula (I) and $L^8$ represents a leaving group;

or (p) preparing a compound of formula (I) wherein $R^2$ represent the same as $R^3$ by reacting a compound of formula $(XII)^2$

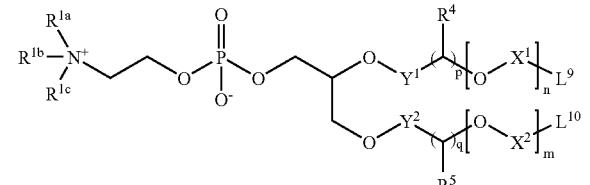

wherein $R^{1a}$, $R^{1b}$, $R^{1c}$, $R^4$, $R^5$, $X^1$, $X^2$, $Y^1$, $Y^2$, m, n, p and q are as defined above for formula (I) and $L^9$ and $L^{10}$ represent leaving groups, with a compound of formula $(XV)^1$ $$R^2OH \qquad (XV)^1$$

or a salt thereof, wherein $R^2$ is as defined above for formula (I); or (q) reacting a compound of formula $(XVI)^1$

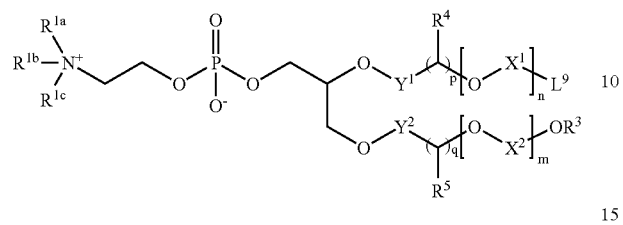

(XVI)$^1$ wherein $R^{1a}$, $R^{1b}$, $R^{1c}$, $R^3$, $R^4$, $R^5$, $X^1$, $X^2$, $Y^1$, $Y^2$, m, n, p, q and $L^9$ are as defined above for formula (I), with a compound of formula $(XV)^1$ or a salt thereof; or (r) reacting a compound of formula $(XVI)^2$

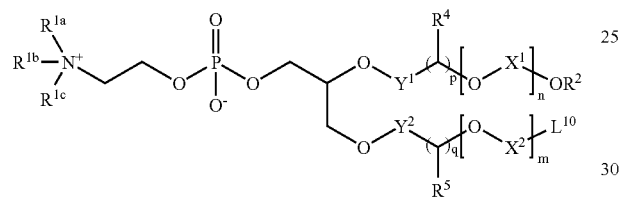

(XVI)$^2$ wherein $R^{1a}$, $R^{1b}$, $R^{1c}$, $R^2$, $R^4$, $R^5$, $X^1$, $X^2$, $Y^1$, $Y^2$, m, n, p, q and $L^{10}$ are as defined above for formula (I), with a compound of formula $(XV)^2$

$R^3OH$     (XV)$^2$ or a salt thereof, wherein $R^3$ is as defined above for formula (I); or (s) preparing a compound of formula (I) wherein $R^{1a}$ represents the same as $R^{1b}$ and $R^{1c}$ by reacting a compound of formula (XVII)

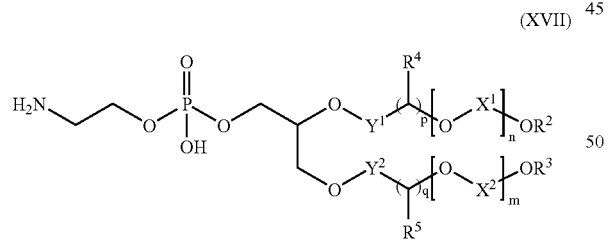

(XVII)

wherein $R^2$, $R^3$, $R^4$, $R^5$, $X^1$, $X^2$, $Y^1$, $Y^2$, m, n, p and q are as defined above for formula (I) with a compound of formula (XVIII)

$R^{1a}L^{11}$     (XVII)

wherein $R^{1a}$ is as defined above for formula (I) and $L^{11}$ represents a leaving group; or (t) preparing a compound of formula (I) wherein $R^2$ and $R^3$ independently represent $C_{1-4}$ alkyl optionally substituted by up to 5 fluorine atoms, by reacting a compound of formula (XIX)

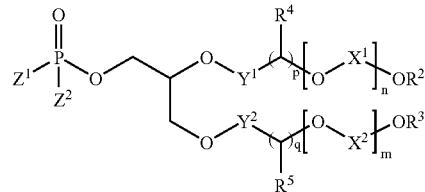

(XIX)

wherein $R^2$ and $R^3$ independently represent $C_{1-4}$ alkyl optionally substituted with up to 5 fluorine atoms and $R^4$, $R^5$, $X^1$, $X^2$, $Y^1$, $Y^2$, m, n, p and q are as defined above for formula (I) and $Z^1$ and $Z^2$ represent a halogen with a compound of formula (XX)

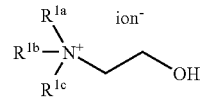

(XX)

wherein $R^{1a}$, $R^{1b}$ and $R^{1c}$ are as defined above for formula (I) and ion$^-$ represents a negative counter ion followed by aqueous work up; or (u) reacting a compound of formula (XXI)

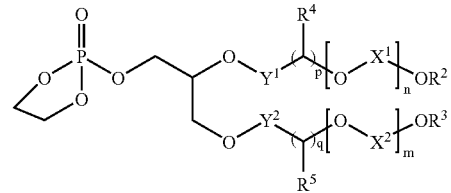

(XXI)

wherein $R^2$, $R^3$, $R^4$, $R^5$, $X^1$, $X^2$, $Y^1$, $Y^2$, m, n, p and q are as defined above for formula (I) with a compound of formula (XXII)

(XXII)

or a salt thereof, wherein $R^{1a}$, $R^{1b}$, and $R^{1c}$ are as defined above for formula (I).

18. A method for the treatment of a condition selected from asthma, COPD and rhinitis comprising administering an effective amount of a pharmaceutical aerosol formulation according to claim 12 to a patient in need thereof.

19. A method for the treatment of a condition selected from asthma, COPD and rhinitis comprising administering an effective amount of a pharmaceutical aerosol formulation according to claim 13 to a patient in need thereof.

20. A method for the treatment of a condition selected from asthma, COPD and rhinitis comprising administering an effective amount of a pharmaceutical aerosol formulation according to claim 14 to a patient in need thereof.

* * * * *